(12) United States Patent
Bertram

(10) Patent No.: US 11,744,973 B2
(45) Date of Patent: Sep. 5, 2023

(54) PUNCTURE CRICOTHYROTOMY SET

(71) Applicant: VBM Medizintechnik GmbH, Sulz a.N. (DE)

(72) Inventor: Volker Bertram, Sulz a.N. (DE)

(73) Assignee: VBM Medizintechnik GmbH, Sulz a.N. (DE)

( * ) Notice: Subject to any disclaimer, the term of this patent is extended or adjusted under 35 U.S.C. 154(b) by 449 days.

(21) Appl. No.: 17/248,272

(22) Filed: Jan. 15, 2021

(65) Prior Publication Data

US 2021/0220593 A1 Jul. 22, 2021

(30) Foreign Application Priority Data

Jan. 16, 2020 (DE) ............... 10 2020 200 502.8

(51) Int. Cl.
*A61M 16/04* (2006.01)

(52) U.S. Cl.
CPC ...... *A61M 16/0472* (2013.01); *A61M 16/045* (2014.02); *A61M 16/0465* (2013.01); *A61M 16/0497* (2013.01)

(58) Field of Classification Search
CPC .. A61M 16/00; A61M 16/0003; A61M 16/04; A61M 16/0402; A61M 16/0465; A61M 16/0472; A61M 16/0488; A61M 16/0497
See application file for complete search history.

(56) References Cited

U.S. PATENT DOCUMENTS

| | | | | |
|---|---|---|---|---|
| 5,546,939 A * | 8/1996 | French | ............... | A61M 16/0472 128/207.29 |
| 6,109,264 A * | 8/2000 | Sauer | .................... | A61M 29/02 128/207.29 |
| 10,105,507 B2 * | 10/2018 | Nhan | ................. | A61M 16/0472 |
| 2009/0163942 A1 * | 6/2009 | Cuevas | ............. | A61M 16/0472 606/167 |
| 2010/0012130 A1 * | 1/2010 | Guerra | ............... | A61M 16/0454 128/207.29 |
| 2010/0275911 A1 * | 11/2010 | Arlow | ................ | A61M 16/0472 128/207.29 |
| 2011/0290245 A1 * | 12/2011 | Cuevas | ................. | A61M 29/02 128/200.26 |
| 2017/0326318 A1 | 11/2017 | Vanner | | |
| 2020/0069900 A1 * | 3/2020 | Rabin | ................. | A61M 16/085 |

FOREIGN PATENT DOCUMENTS

DE     20 2017 002 009 U1     7/2017

* cited by examiner

*Primary Examiner* — Colin W Stuart
(74) *Attorney, Agent, or Firm* — ORBIT IP

(57) ABSTRACT

A puncture cricothyrotomy set includes a tracheal tube and a puncture cannula arranged therein, which has a rotary actuating device with a handle. By moving the handle about its rotational axis, the puncture cannula can be moved from its puncture position into the tracheal tube far enough that the tip section is arranged completely within the tracheal tube.

15 Claims, 5 Drawing Sheets ns
PUNCTURE CRICOTHYROTOMY SET

CROSS-REFERENCE TO RELATED APPLICATIONS

This application claims priority to German Patent Application No. 10 2020 200 502.8, filed Jan. 16, 2020, the entire contents of which are hereby incorporated in full by this reference.

DESCRIPTION

Field of the Invention

The present invention relates to cricothyrotomy. More particularly, the present invention relates to a puncture cricothyrotomy set.

Background of the Invention

In the case of life-threatening obstructions of the airways that make spontaneous breathing and/or ventilation or intubation impossible, cricothyrotomy is an invasive emergency measure for ensuring patient oxygenation. In cricothyrotomy, the cricothyroid ligament, which is a taut membrane between the cricoid and thyroid cartilage, is opened percutaneously, i.e. from the outside. In emergency medicine, puncture cricothyrotomy sets are generally used for this purpose which are kept sterile packed for such cases. The cricothyrotomy sets available on the market generally have a tracheal tube with a breathing lumen which has a proximal and a distal opening. A puncture cannula is used to puncture the trachea. When the cricothyrotomy set is ready for puncture, i.e. when the puncture cannula is arranged in the puncture position, the puncture cannula extends along the breathing lumen through the tracheal tube and its tip segment protrudes distally beyond the tracheal tube. Emergency cricothyrotomies have a considerable complication rate even when using such prefabricated sets. Dangerous acute complications such as bleeding and injuries to other organ structures can occur. In addition, it should be noted that the cricothyrotomy is always an exceptional situation for the doctor performing the procedure and, as a non-elective procedure, is usually not part of routine medical measures. With conventional puncture cricothyrotomy sets, for example, the puncture cannula has to be manually withdrawn from the tracheal tube after the trachea has been punctured and after a positive aspiration test using a syringe connected to the proximal end of the puncturing cannula. Because of the frictional engagement between the tracheal tube and puncture cannula, the tracheal tube must be very carefully secured in its relative position on the patient to prevent it from accidentally slipping out of the stoma. This is not always reliably successful in stressful emergency situations and in the presence of blood. As a result, the tracheal tube can be dislocated from the trachea, for example.

It is therefore the object of the invention to provide a puncture cricothyrotomy set which is easier to use, even for the inexperienced, and which offers an even greater degree of patient safety. This object is achieved by a puncture cricothyrotomy set with the features specified in claim 1.

SUMMARY OF THE INVENTION

The puncture-cricothyrotomy set according to the invention (hereinafter referred to as "cricothyrotomy set," for short) has a rotary actuating device with a handle that can be moved about a rotational axis, by means of which the tip section of the puncture cannula can be moved, preferably solely, by rotating the handle about its rotational axis, far enough back into or into the tracheal tube from its aforementioned puncture position that the tip section of the puncture cannula is arranged completely or almost completely inside the tracheal tube. Here the puncture cannula is in its inactive position or in its position protected by the tracheal tube. As a result, undesired jerky movements of the tracheal tube and of the puncture cannula arranged in the puncture position can be prevented in a simple and reliable manner. The risk of damage to organ structures due to the tip section of the puncture cannula, which is usually provided with a cut, as well as dangerous dislocation of the previously intratracheally positioned tracheal tube can thereby be reduced.

From a manufacturing point of view, the rotary actuating device is preferably arranged on the proximal end section of the puncture cannula. As a result, after the puncture cannula has been used once, the rotary actuating device can be disposed of in a simple manner together with the puncture cannula. The tracheal tube and its handling do not differ from conventional tracheal tubes.

According to the invention, the rotary actuating device is preferably provided with a cam which cooperates with the tracheal tube, in particular with its proximal end. Such a cam can also be manufactured in a simple and cost-effective manner in terms of manufacturing technology and allows a high degree of mechanical functional reliability. The proximal end of the tracheal tube is usually provided with or has a connector for connecting a ventilation bag or a ventilation device. The connector can in particular be inserted into the tracheal tube via the proximal opening of the breathing lumen of the tracheal tube. The connector preferably comprises a relatively hard material that is not easily deformed, so that the cam of the rotary actuating device can be supported on this connector.

According to the invention, the cam can be molded onto the handle. The handle and the cam are thus designed together in one piece. This offers manufacturing advantages. In addition, a particularly high level of patient safety can be achieved in this way. Further, the cam can be part of a cam curve. With a corresponding shaping of the cam curve, the tip section of the puncture cannula can be moved into and out of the tracheal tube with little effort and largely or even completely jerk-free when the handle is adjusted.

The handle can be designed, for example, in the form of a knurled wheel, a single-armed or multi-armed lever, or even in the form of a free-form handle. Other shapes of the handle that allow the handle to be operated with one finger or with several fingers of the human hand are possible.

The rotary actuating device particularly preferably has markings that can be used to read the specific functional position of the rotary actuating device relative to the puncture cannula. The markings are preferably embodied in different colors/geometries. Using the markings, the current position of the puncture cannula relative to the tracheal tube can be detected in a simple manner.

The rotary actuating device preferably comprises plastic and in particular can be designed as an injection molded part.

According to a preferred further development of the invention, the rotary actuating device can have a double function and can also lock the puncture cannula arranged in the puncture position relative to the tracheal tube. For example, the rotary actuating device can in particular have a first locking means which engages in a second locking means of the tracheal tube when the handle is in the first functional position and when the puncture cannula is arranged in the puncture position. In this way, the puncture cannula is releasably locked in the puncture position and cannot be displaced on the tracheal tube.

According to the invention, the first locking means can be designed as a profile projection, in particular of the handle, while the second locking means is designed as a lateral recess, for example in the form of an outwardly open blind hole, in the wall of the tracheal tube or the aforementioned connector. If the recess is arranged at the proximal end of the tracheal tube or on the connector, the functionality of the tracheal tube/connector can be fully retained thereby without disadvantages.

The tracheal tube advantageously has a cannula shield, known per se, for fixing the tracheal tube to the person to be supplied with the tracheal tube and can additionally have a depth stop element for limiting the maximum insertion depth of the tracheal tube during the puncture process. The depth stop element is detachably arranged on the tracheal tube, in particular clipped to it, along the tracheal tube between said cannula shield and the distal opening of the breathing lumen or the distal end of the tracheal tube. The tracheal tube can also be provided with a lockable cuff (=cuff). The cuff is preferably designed as a low-pressure cuff.

The tip section of the puncture cannula preferably has an (outer) jacket surface that is convexly curved towards the tip and a lateral concave cut which can extend to the tip of the tip section. Overall, this can achieve a cutting perforation of the stoma to be produced and a (non-cutting) widening of the stoma to be produced to the minimum size required for the passage of the tracheal tube. The risk of an overly large stoma with the associated risk of tearing the trachea or damaging other organ structures can thereby be reduced.

In order to ensure a sufficiently effective expansion of the tissue delimiting the stoma, according to the invention, the concave cut of the tip section preferably does not extend in the radial direction beyond the center axis of the tip section.

According to the invention, the tip section of the puncture cannula can be angled with respect to the distal longitudinal segment of the puncture cannula directly adjoining the tip section. In other words, the center axis of the tip section and the longitudinal axis or the radius of the remaining distal longitudinal segment of the puncture cannula together form an angle α where α<180°. The center axis of the puncture cannula comprises the tip of the tip section.

Further advantages of the invention result from the description and the drawings. The embodiments shown and described are not to be understood as an exhaustive enumeration but rather have exemplary character for the description of the invention.

BRIEF DESCRIPTION OF THE DRAWINGS

The invention is explained in greater detail below with reference to an exemplary embodiment shown in the drawing. In the drawings.

DETAILED DESCRIPTION OF THE PREFERRED EMBODIMENTS

Figure 1:
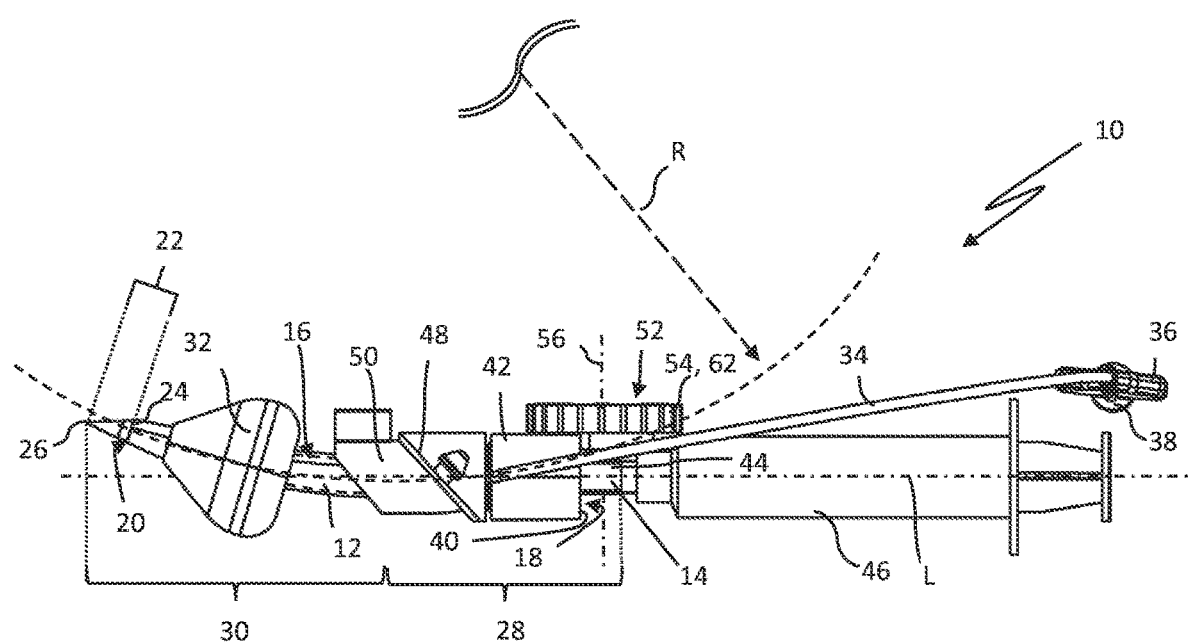
FIG. 1 is a side view of a ready-to-use puncture cricothyrotomy set with a tracheal tube and a puncture cannula arranged in the tracheal tube in the puncture position, which can be moved distally back into the tracheal tube by means of a rotary actuating device, and with a syringe connected to the puncture cannula.
Figure 2:
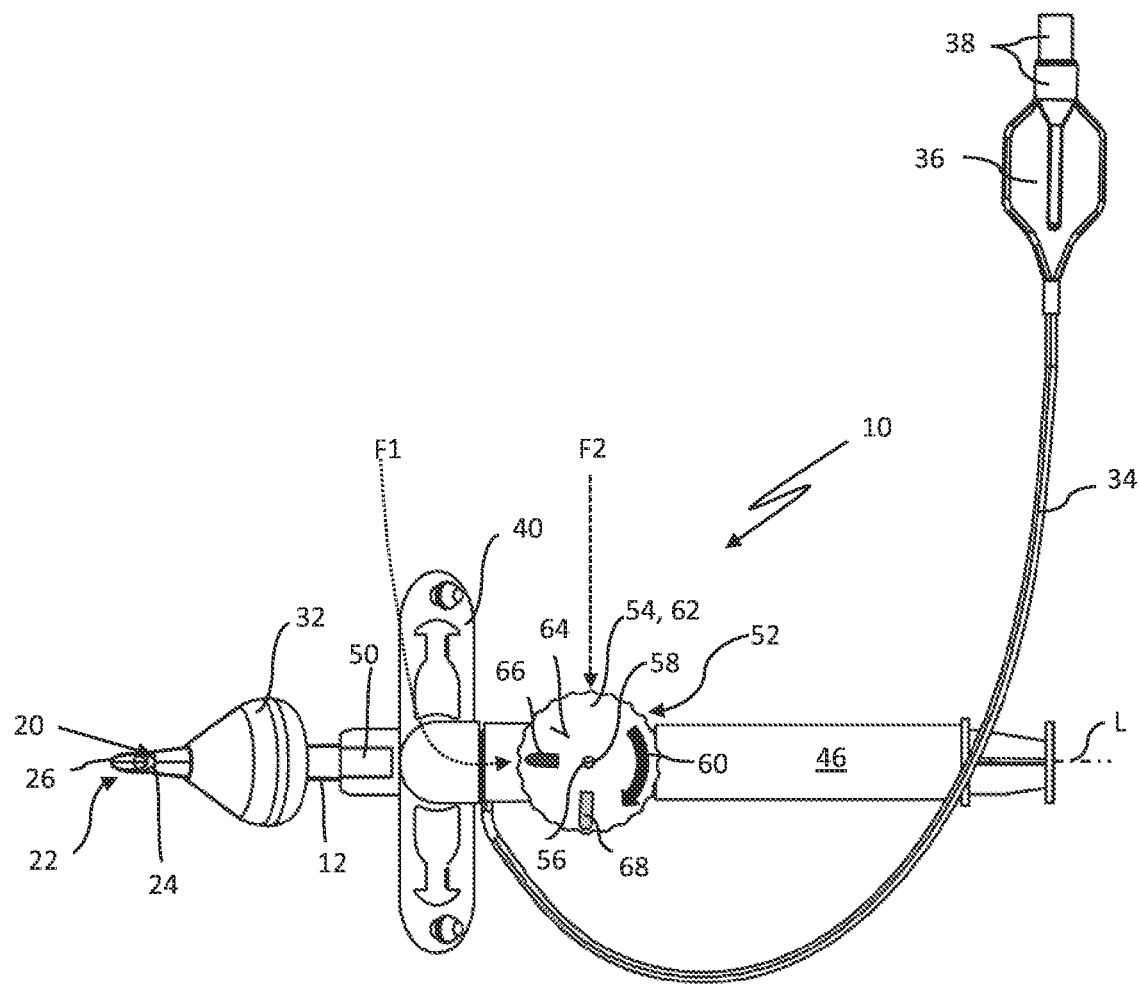
FIG. 2 illustrates the puncture cricothyrotomy set according to FIG. 1 in a top plan view of the handle of the rotary actuating device with a representation of markings arranged thereon.
Figure 3:
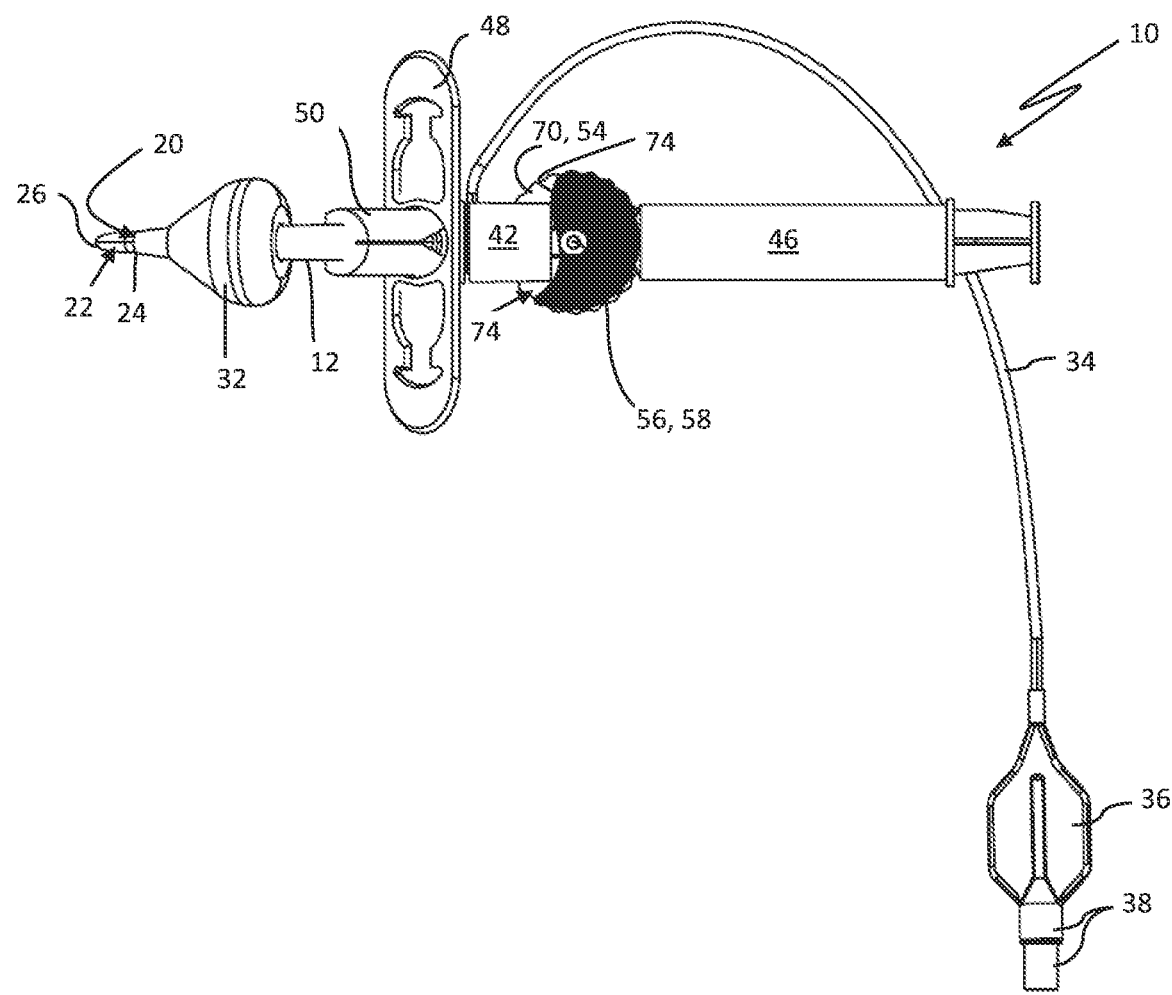
FIG. 3 illustrates the puncture-cricothyrotomy set according to FIG. 1 in a view of the underside thereof with a representation of a cam curve formed on the handle of the rotary actuating device.

FIGS. 1 to 3 show different side views of a puncture cricothyrotomy set 10 for securing the airway in humans in emergency situations. The cricothyrotomy set 10 is shown ready for use or puncture. The cricothyrotomy set 10 comprises a tracheal tube 12 and a puncture cannula 14. The puncture cannula 14 is arranged in its puncture-ready position relative to the tracheal tube 12 (=puncture position). The tracheal tube 12 comprises a breathing lumen 16 illustrated with a dashed line in FIG. 1 and with a proximal and a distal opening 18, 20.

In its puncture position shown in FIG. 1, the puncture cannula 14 extends over the proximal opening 18 of the breathing lumen 16 into the tracheal tube 12 and along the breathing lumen 16 through the tracheal tube 12. The (distal) tip section 22 of the puncture cannula 14 protrudes beyond the distal end 24 of the tracheal tube, i.e. beyond the distal opening 20 of the breathing lumen 16 out of the tracheal tube 12. The tip of the puncture cannula 14 is denoted by 26.

The tracheal tube 12 and the puncture cannula 14 each have a proximal length segment 28 and an adjoining distal length segment 30. The proximal length segments 28 are each straight and run along a common longitudinal axis L. The distal length segments 30 are each curved and have a matching or substantially matching radius R (FIG. 2).

The tracheal tube 12 can be provided with an inflatable cuff 32, also referred to as a cuff, in a manner known per se. Such a cuff 32 is shown in FIG. 1 in the inflated state. Via a hose 34, the cuff 32 is provided with a pilot balloon 36 and a valve connector 38 for connecting a syringe or a cuff pressure gauge with a pump (not shown in the drawing). The cuff 32 is preferably designed as a so-called low-pressure cuff.

At its proximal end 40, the tracheal tube 12 has a connector 42, here a 15 mm standard connector, for connecting a ventilation bag or a ventilation device (not shown). The connector 42 is preferably arranged in the tracheal tube 12 in a press fit manner.

A syringe 46 is connected to the proximal end section 44 of the puncture cannula 14. With the syringe 46, the correct puncture depth of the puncture cannula 14, and thus, indirectly, an intratracheal position of the tube tip can be verified by aspirating tracheal air. After the tracheal tube 12 has been positioned in its intended intratracheal position, a second syringe, which is enclosed with the sterile packaged cricothyrotomy set 10, is used to inflate the cuff 24. To fix the position of the tracheal tube 12 on the neck of a person to be supplied with the tracheal tube (not shown in the drawing), the tracheal tube 12 has a so-called cannula shield 48 to which can be attached a strap or the like that can be guided around the neck. The cannula shield 48 can be fixed in a non-displaceable manner on the tracheal tube 12 at different longitudinal positions in a manner known per se for individually placing the tracheal tube and fixing the latter in position on the neck of the person being supplied therewith (not shown).

During the puncturing process, a depth stop element 50 limits the maximum possible penetration or puncture depth of the tracheal tube 12 reinforced by the puncture cannula 14. The depth stop element 50 is releasably attached to the tracheal tube 12 and can be clipped thereto, for example, along the tracheal tube 12 between the cuff 32 and the cannula shield 48. The depth stop element 50 can be supported proximally directly on the cannula shield 48. After the trachea of a person to be supplied with the tracheal tube 12 has been punctured, the depth stop element 50 is released or removed from the tracheal tube 12, so that the tracheal tube 12 can be pushed further into the trachea until it comes to rest in its intended intratracheal position and the cannula shield 48 is positioned against the outside of the neck.

When an emergency cricothyrotomy is performed, loosening and partially moving the tip section 22 of the puncture cannula 14 back into the tracheal tube 12 already positioned intratracheally is particularly risky. The distal end 24 of the tracheal tube 12 surrounds the puncture cannula 14 in a positive fit and, as a rule, also in a non-positive fit, so that jerky movements of the puncture cannula 14 can occur again and again. As a result, on the one hand there is the risk of inadvertent damage to organ structures or of the tracheal tube 12 unintentionally slipping out of the intratracheal position it has already reached. The cricothyrotomy set 10 therefore has a rotary actuating device 52 which facilitates disconnecting of the puncture cannula 14 and tracheal tube 12. The rotary actuating device 52 is arranged here on the proximal end section 44 of the puncture cannula 14 and comprises a handle 54. The handle can be moved about a rotational axis 56 relative to the puncture cannula 14. An axle piece 58 fastened to the puncture cannula is used to fasten the handle to the puncture cannula 14. The rotational axis 56 is oriented to run orthogonally to the longitudinal axis L or in its projection to the longitudinal axis L. In FIGS. 1 to 3, the handle 54 is shown in its first rotational or functional position $F_1$.

The puncture cannula 14 can be moved with its tip section 22 in the direction of arrow 60 out of its puncture position shown in FIG. 1 into the tracheal tube 12 such that the tip section 22 is arranged, preferably completely, within the tracheal tube 12 solely by rotating the handle 54 (FIG. 2) from its first functional position $F_1$ to its second functional position $F_2$. This corresponds to a protective position of the puncture cannula 14 made possible by the tracheal tube 12. Only then is the tracheal tube 12 pushed into the trachea until the cannula shield 48 is in contact with the skin of the person supplied with the tracheal cannula. The tracheal tube 12 is then finally secured in its predetermined position by fixing the cannula shield 48 on the neck and is now available as an artificial respiratory opening for oxygenating the person.

According to FIGS. 1 to 3, the handle 54 can be designed in the form of a knurled wheel 62. It is understood, however, that the handle 54 can also have a different shape. For example, the handle 54 can be designed as a one-armed or multi-armed lever (not shown in the drawing), as is known from one-way or multi-way taps used in infusion therapy. According to FIG. 2, the handle 54 has a first and a second marking 66, 68 on its upper side 64 in order to visually indicate the respective functional position $F_1$, $F_2$ of the rotary actuating device 52 to the user.

According to the plan view of the underside 70 of the handle 54 in FIG. 3, the rotary actuating device 52 has an actuating member in the form of a cam 72, which is coupled in terms of movement to the handle 54. The actuating member or the cam 72 cooperates with the proximal end 40 of the tracheal tube 12, i.e. the connector 42, in this case. The cam 72 can be part of a cam or control curve 74 which can be molded onto the handle 54.

Figure 4:
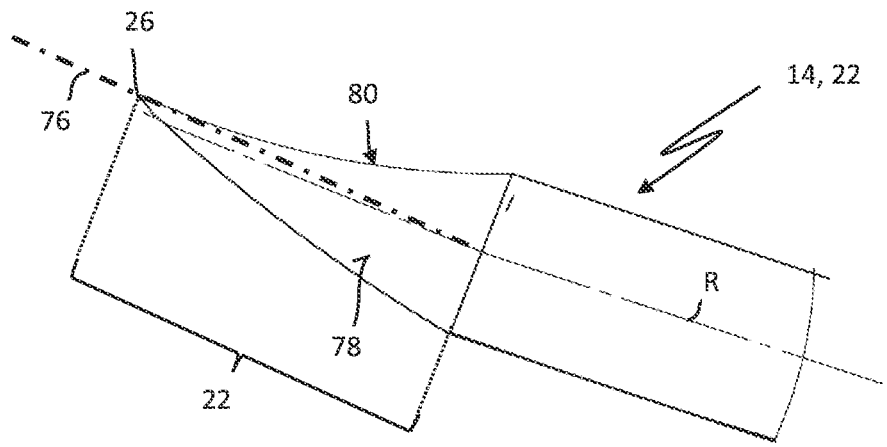
FIG. 4 is a detailed view of the tip section of the puncture needle of the puncture cricothyrotomy set according to FIG. 1.
Figure 5:
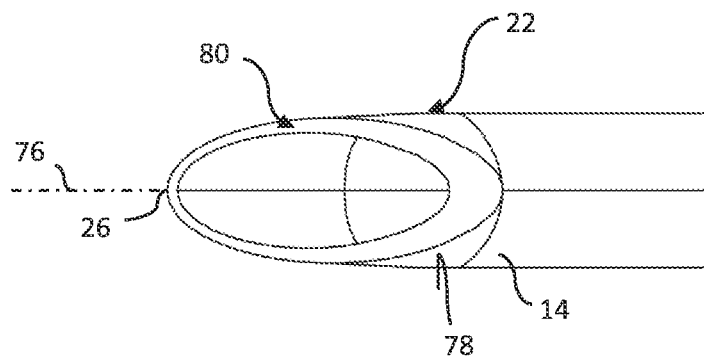
FIG. 5 is a further detailed view of the tip section of the puncture needle of the puncture cricothyrotomy set according to FIG. 1.
Figure 6:
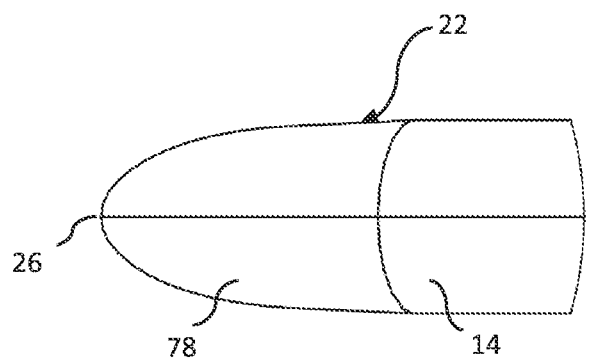
FIG. 6 is a further detailed view of the tip section of the puncture needle of the puncture cricothyrotomy set according to FIG. 1.

In FIGS. 4 to 6, the tip section 22 of the puncture cannula 14 is shown in different side views. The tip section 22 is angled with respect to the remaining distal longitudinal segment 30 of the puncture cannula 14. In other words, the tip section has a center axis 76 which, with the radius R of the remaining distal longitudinal segment 30, forms an angle $\alpha$ with $\alpha < 180°$. The center axis 76 comprises the tip 26 of the puncture cannula 14.

The tip section 22 has a paraboloid basic shape around part of its circumference with a jacket surface 78, which is convexly curved outwards towards the tip 26.

The tip section 22 is provided with a lateral concave cut 80, which can extend to the tip 26 according to FIG. 5. Overall, a cutting perforation of the stoma to be produced (artificial respiratory opening) and a (non-cutting) widening of the stoma to be produced to the minimum size required for the passage of the tracheal tube 12 can thereby be achieved. The risk of the stoma being overly large with the associated risk of tearing the trachea or damaging other organ structures can thereby be reduced. The concave cut 80 according to FIG. 4 does not extend in the radial direction beyond the center axis 76 of the tip section 22 in order to thus ensure a sufficiently effective expansion of the tissue delimiting the stoma.

Figure 7:
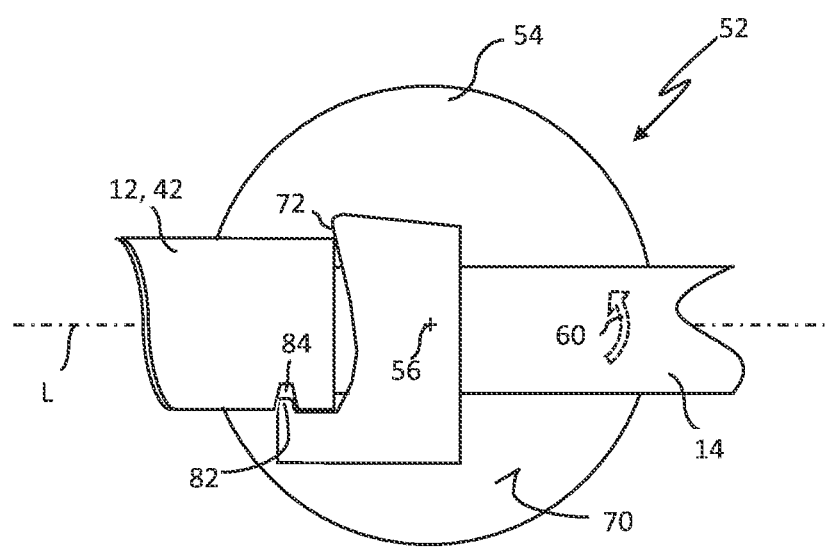
FIG. 7 is a detailed view of a further exemplary embodiment of the cricothyrotomy set, in which the rotary actuating device is additionally set up for non-displaceably and releasably fixing the puncture cannula arranged in the puncture position relative to the tracheal tube.

According to FIG. 7, the rotary actuating device 52 can be designed to lock the puncture needle 14 arranged in the puncture position relative to the tracheal tube 12. For this purpose, the rotary actuating device 52 has a first locking means 82, here in the form of a profile projection of the handle 54 or the cam curve 74 (FIG. 3). In the first functional position $F_1$ of the handle 54, the first locking means 82 engages in a second locking means 84, here a lateral recess or a blind hole on the connector 42 of the tracheal tube 12. As a result, the tracheal tube 12 and the puncture cannula 14 are locked together in a non-displaceable manner. By rotating the handle 54 from the first functional position $F_1$ to the second functional position $F_2$, the locking is forcibly released and the puncture cannula 14 with its tip section 22 is moved back into the tracheal tube 12 by moving the cam 72 against the proximal end of the tracheal tube 12.

What is claimed is:
1. A puncture cricothyrotomy set, comprising:
a tracheal tube which has a breathing lumen with a proximal and a distal opening; and
a puncture cannula, which when the cricothyrotomy set is ready for puncture extends along the breathing lumen through the tracheal tube and protrudes with its tip section distally beyond the tracheal tube;

wherein the puncture cannula has a rotary actuating device with a handle that can be moved about a rotational axis, by means of which the puncture cannula with its tip section can be moved, by rotating the handle, far enough into the tracheal tube from its puncture position that the tip section is arranged completely inside the tracheal tube.

2. The puncture cricothyrotomy set according to claim 1, wherein the rotary actuating device is arranged on a proximal end section of the puncture cannula.

3. The puncture cricothyrotomy set according to claim 2, wherein the rotary actuating device has a cam which cooperates with a proximal end of the tracheal tube.

4. The puncture cricothyrotomy set according to claim 3, wherein the cam is molded onto the handle.

5. The puncture cricothyrotomy set according to claim 4, wherein the cam is part of a cam curve.

6. The puncture cricothyrotomy set according to claim 3, wherein the cam is part of a cam curve.

7. The puncture cricothyrotomy set according to claim 1, wherein the handle has markings that can be used to read a specific functional position of the handle.

8. The puncture cricothyrotomy set according to claim 1, wherein the puncture cannula can be releasably locked in its puncture position relative to the tracheal tube by means of the rotary actuating device.

9. The puncture cricothyrotomy set according to claim 8, wherein the rotary actuating device has a first locking means which engages in a second locking means of the tracheal tube in a first functional position and when the puncture cannula is arranged in the puncture position.

10. The puncture cricothyrotomy set according to claim 1, wherein the tip section has a jacket surface curved convexly outward towards a tip of a puncture cannula and a lateral concave cut.

11. The puncture cricothyrotomy set according to claim 10, wherein the concave cut extends to the tip of the puncture cannula.

12. The puncture cricothyrotomy set according to claim 11, wherein the concave cut does not overlap a center axis of the tip section in a radial direction.

13. The puncture cricothyrotomy set according to claim 10, wherein the concave cut does not overlap a center axis of the tip section in a radial direction.

14. The puncture cricothyrotomy set according to claim 1, wherein the tracheal tube has a cannula shield and additionally a depth stop element for limiting the maximum insertion depth of the puncture cannula during a puncture process, wherein the depth stop element is arranged along the tracheal tube, by being clipped thereto, between the cannula shield and a distal end of the tracheal tube or an inflatable cuff of the tracheal tube.

15. The puncture cricothyrotomy set according to claim 1, wherein the rotary actuating device has a cam which cooperates with a proximal end of the tracheal tube.

* * * * *

UNITED STATES PATENT AND TRADEMARK OFFICE
CERTIFICATE OF CORRECTION

| | |
|---|---|
| PATENT NO. | : 11,744,973 B2 |
| APPLICATION NO. | : 17/248272 |
| DATED | : September 5, 2023 |
| INVENTOR(S) | : Volker Bertram |

It is certified that error appears in the above-identified patent and that said Letters Patent is hereby corrected as shown below:

In the Claims

Column 8, Claim 10, Line 6, "of a" should read --of the--.

Signed and Sealed this
Twenty-fourth Day of October, 2023

Katherine Kelly Vidal
*Director of the United States Patent and Trademark Office*